United States Patent [19]

Umezawa et al.

[11] 4,107,424
[45] Aug. 15, 1978

[54] 1-N-[(S)-α-HYDROXY-ω-AMINOACYL] DERIVATIVES OF 3',4'-DIDEOXYKANAMYCIN B AND 3'-DEOXYKANAMYCIN B ANTIBIOTICS

[75] Inventors: Hamao Umezawa; Sumio Umezawa; Kenji Maeda, all of Tokyo; Osamu Tsuchiya; Shinichi Kondo, both of Yokohama; Shunzo Fukatsu, Tokyo, all of Japan

[73] Assignee: Zaidan Hojin Biseibutsu Kagaku Kenkyu Kai, Tokyo, Japan

[21] Appl. No.: 708,076

[22] Filed: Jul. 23, 1976

Related U.S. Application Data

[63] Continuation of Ser. No. 402,085, Oct. 1, 1973, Pat. No. 4,001,200.

[30] Foreign Application Priority Data

Oct. 6, 1972 [JP] Japan .............................. 47-99866
Oct. 19, 1972 [JP] Japan ............................ 47-103988
Dec. 11, 1972 [JP] Japan ............................ 47-123482
Jan. 23, 1973 [JP] Japan ................................ 48-9146

[51] Int. Cl.² .................... C07H 15/22; A61K 31/70
[52] U.S. Cl. ...................................... 536/10; 424/180
[58] Field of Search ............................................ 536/10

[56] References Cited
U.S. PATENT DOCUMENTS 3,753,973  8/1973  Umezawa et al. .................... 536/10
3,781,268  12/1973  Kawaguchi .......................... 536/10

OTHER PUBLICATIONS

Umezawa, "3',4'-Dideoxy Kanamycin B ... Aeruginosa", J. of Antibiotics, 24, No. 7, pp. 485–487.
Journal of Antibiotics, vol. 26, No. 11, Jul. 1973, pp. 412–414 and 705–707.

Primary Examiner—Natalie Trousof
Assistant Examiner—Cary Owens
Attorney, Agent, or Firm—Haight & Huard

[57] ABSTRACT

A new and useful 1-N-[(S)-α-hydroxy-ω-aminoacyl] derivative of an aminoglycosidic antibiotic, including its deoxy derivative, such as kanamycin B, 3'-deoxyneamine, 3',4'-dideoxyneamine, 3',4'-dideoxyribostamycin or 3',4'-dideoxykanamycin B is now synthetized from the parent substance, aminoglycosidic antiobiotic. The new 1-N-[(S)-α-hydroxy-ω-aminoacyl] derivative shows a wider and/or higher antibacterial activity than the parent substance and is useful in the treatment of infections by gram-negative and gram-positive bacteria, including drug-resistant strains thereof. The preparation of this new derivative may be made by 1-N-acylating the parent aminoglycosidic antibiotic with (S)-α-hydroxy-ω-aminocarboxylic acid with the amino group being protected, and chromatographically separating the acylated products to isolate the desired 1-N-acyl derivative, followed by the removal of the amino-protecting group.

5 Claims, No Drawings

1-N-[(S)-α-HYDROXY-ω-AMINOACYL] DERIVATIVES OF 3',4'-DIDEOXYKANAMYCIN B AND 3'-DEOXYKANAMYCIN B ANTIBIOTICS

This is a continuation, of application Ser. No. 402,085, filed Oct. 1, 1973 and now U.S. Pat. No. 4,001,200.

This invention relates to new and useful 1-N-[(S)-α-hydroxy-ω-aminoacyl] derivatives of an aminoglycosidic antibiotic such as kanamycin B, 3'-deoxyneamine, 3',4'-dideoxyneamine, 3',4'-dideoxyribostamycin or 3',4'-dideoxykanamycin B. This invention further relates to a process for the production of the 1-N-[(S)-α-hydroxy-ω-aminoacyl] derivative of the aminoglycosidic antibiotic.

Kanamycins and neamine are well known aminoglycosidic antibiotics, and ribostamycin is also a known aminoglycosidic antibiotic, originally designated as vistamycin or Antibiotic SF-733; see "The Journal of Antibiotics" Vol. 23, No. 3, pages 155-161 and No. 4, pages 173-183(1970). This ribostamycin has been identified as 5-0-β-D-ribofuranosyl-neamine. These aminoglycosidic antibiotics have been used widely as valuable, chemotherapeutic agents, but drug-resistant strains which are resistant to these known aminoglycosidic antibiotics have occurred in recent years. Accordingly, the mechanism of resistance of these drug resistant bacteria to the known aminoglycosidic antibiotics has been studied. For instance, one of the present inventors, H. Umezawa et al have found that some strains of gram-negative bacteria carrying R factor, *Staphylococcus aureus and Pseudomonas aeruginosa* isolated from patients, are resistant to kanamycins and that these kanamycin-resistant strains have a mechanism of resistance in that they produce an enzyme capable of phosphorylating the 3'-hydroxyl group of kanamycins and inactivate the kanamycins with the aid of phosphotransferase activity; see "Science" Vol. 157, page 1559 (1967).

On the basis of this finding, H. Umezawa et al have prepared semi-synthetically 3'-deoxykanamycin and 3',4'-dideoxykanamycin B wherein the 3'-hydroxyl group of the kanamycin molecule has been removed therefrom, as well as 3',4'-dideoxyneamine and 3',4'-dideoxyribostamycin as described in the "Journal of antibiotics" Ser. A, Vol. 21, pages 274-275(1971); Vol. 24, pages 485-487; Vol. 24, pages 711-712(1971) and Vol. 25, pages 613-617(1972). 3'-deoxyneamine has also been prepared (Japanese patent application No. 122436/1972 filed on 8th December, 1972). 3'-deoxykanamycin; 3',4'-dideoxykanamycin B; 3'-deoxyneamine; and 3',4'-dideoxyneamine are actually effective against the above-mentioned kanamycin-resistant strains, but 3',4'-dideoxyribostamycin has been inactivated by phosphorylating 5"-hydroxyl group of this antibiotic with the aid of phosphotransferase. Furthermore, these deoxy derivatives of kanamycins have been found to be inactive against other kanamycin-resistant strains such as *Escherichia coli* JR66/W677 which has been transferred R factor from clinically isolated Klebsiella. H. Umezawa et al have found that the latter kind of kanamycin-resistant strains have a mechanism of resistance in that they produce an enzyme capable of adenylylating the 2"-hydroxyl group of the kanamycin or 3',4'-dideoxykanamycin B molecule with ATP (adenosine triphosphate) and inactivate kanamycin and 3',4'-dideoxykanamycin B by the action of this nucleotidyl-transferase; see the "Journal of Antibiotics" Vol. 24, pages 911-913 (1971) and "Journal of Antibiotics" Vol. 25, page 492 (1972).

On the other hand, it is known that butirosin B which is an aminoglycosidic antibiotic produced by a *Bacillus* species is active against some kanamycin- and ribostamycin-resistant bacteria. Butirosin B has been identified as 1-N-[(S)-α-hydroxy-γ-amino-n-butyryl]-ribostamycin; see the "Tetrahedron Letters" Vol. 28, page 2125 and pages 2617-2630 (1971) and German "Offenlegungsschrift" No. 1914527. From a comparison of the antibacterial activity of ribostamycin with that of butirosin B, we have found that the (S)-4-amino-2-hydroxyl-butyryl substituent on the 1-amino group of the butirosin B molecule has an important role in enabling the ribostamycin to be active even against the ribostamycin-resistant and -sensitive strains, and that the presence of the (S)-4-amino-2-hydroxyl-butyryl substituent at the 1-amino group of the butirosin B molecule can inhibit the action of the nucleotidyl-transferase produced by the kanamycin-resistant strains. From the above findings, we had an expectation that, in general, an 1-N-[(S)-α-hydroxy-ω-aminoacyl] derivative of the aminoglycosidic antibiotics or their deoxy-derivatives would be usefully effective against the drug-resistant bacteria, if it could be synthetized. Accordingly, we have made our further research in an attempt to produce such new 1-N-[(S)-α-hydroxy-ω-aminoacyl]-derivatives of kanamycin B, 3'-deoxyneamine, 3',4'-dideoxyneamine, 3',4'-dideoxyribostamycin and 3',4'-dideoxykanamycin B.

An object of this invention, therefore, is to provide a new and useful 1-N-[(S)-α-hydroxy-ω-aminoacyl]-derivative of the known aminoglycosidic antibiotics or their deoxy-derivatives which is effective even against the strains resistant to the aminoglycosidic antibiotics and their known deoxy-derivatives. Another object of this invention is to provide a process for the production of such a new and useful derivative of the known aminoglycosidic antibiotics and their known deoxy-derivatives. Other objects of this invention will be clear from the following description.

As a result of our extensive research, we have now succeeded in synthetizing a 1-N-[(S)-α-hydroxy-ω-aminoacyl]-derivative of kanamycin B, 3',4'-deoxykanamycin B, 3'-deoxyneamine, 3',4'-dideoxyneamine, 3',4'-dideoxyribostamycin and the like, and we have now found that the new aminoacyl derivative so synthetized exhibits a useful antibacterial activity against the bacteria sensitive to the known aminoglycosidic antibiotics, as well as against the bacteria resistant to the known aminoglycosidic antibiotics, including the deoxy-derivatives thereof.

According to a first aspect of this invention, therefore, there is provided an 1-N-[(S)-α-hydroxy-ω-aminoacyl] derivative of an aminoglycosidic antibiotic, including the deoxy-derivative of said antibiotic, of the following formula:

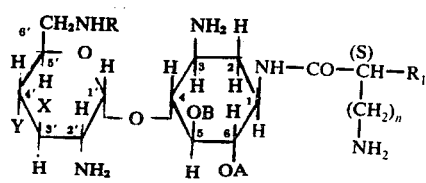 (I)

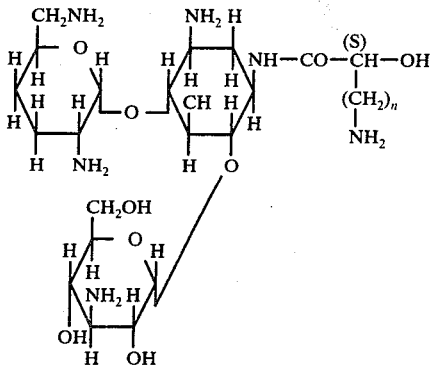 (Ib)

wherein R is a hydrogen atom or an alkyl group of 1–4 carbon atoms; $R_1$ is a hydroxyl group; A is a hydrogen atom or 3-amino-3-deoxy-α-D-glucopyranosyl group of the formula:

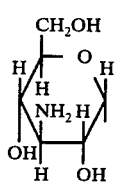

B is a hydrogen atom or β-D-ribofuranosyl group of the formula:

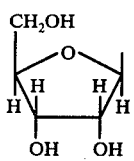

X is a hydrogen atom or hydroxyl group; Y is a hydrogen atom or hydroxy group; and n is an integer of 2 or 3, provided that both of X and Y do not represent simultaneously a hydroxyl group when A is a hydrogen atom and B is a hydrogen atom or β-D-ribofuranosyl group; and the pharmaceutically acceptable acid-addition salts thereof.

According to a first embodiment of the first aspect of this invention, there is provided an 1-N-[(S)-α-hydroxy-ω-aminoacyl]-3',4'-dideoxyneamine or -3',4'-dideoxyribostamycin of the formula:

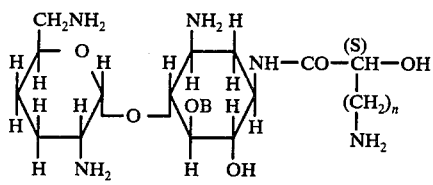 (Ia)

wherein n is an integer of 2 or 3; and B is a hydrogen atom or β-D-ribofuranosyl group, and the pharmaceutically acceptable acid-addition salts thereof. In the 3',4'-dideoxyneamine of the formula (Ia), B is hydrogen. In the 3',4'-dideoxyribostamycin of the formula (Ia), B is β-D-ribofuranosyl group.

According to a second embodiment of the first aspect of this invention, there is provided 1-N-[(S)-4-amino-2-hydroxy-n-butyryl]-3',4'-dideoxykanamycin B of the formula:

and the pharmaceutically acceptable acid-addition salts thereof.

According to a third embodiment of the first aspect of this invention, there is provided an 1-N-[(S)-α-hydroxy-ω-aminoacyl]-3'-deoxyneamine or 3'-deoxyribostamycin or -3'-deoxykanamycin B or -3'-deoxy-6'-N-alkylkanamycin B of the formula:

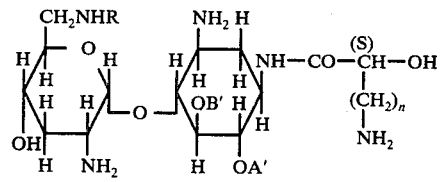 (Ic)

wherein R is a hydrogen atom or an alkyl group of 1–4 carbon atoms; A' is a hydrogen atom or 3-amino-3-deoxy-α-D-glucopyranosyl group; B' is a hydrogen atom or β-D-ribofuranosyl group; and n is an integer of 2 or 3 and particularly a numeral of 2, provided that when A' is the 3-amino-3-deoxy-α-D-glucopyranosyl group, B' is a hydrogen atom, and provided that when R is an alkyl group, A' is the 3-amino-3-deoxy-α-D-glucopyranosyl group; and the pharmaceutically acceptable acid-addition salts thereof.

According to a fourth embodiment of the first aspect of this invention, there is provided 1-N-[(S)-4-amino-2-hydroxybutyryl]-kanamycin B of the formula:

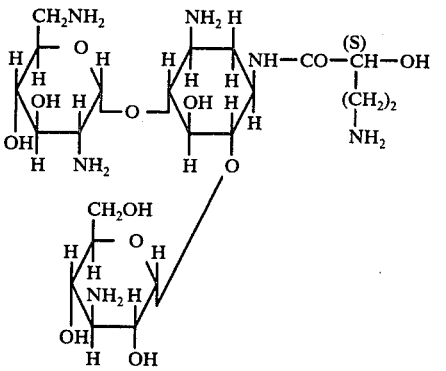 (Id)

and the pharmaceutically acceptable acid-addition salts thereof. The symbol (S) shown in the formulae (I) to (Id) is an expression of the configuration of organic compounds; see R.S. Cahn, C. K. Ingold & V. Prelog; "Experientia" Vol. 12, pages 81–94 (1956).

As suitable examples of the new compounds of the general formula (I) according to this invention are mentioned the following compounds: (1) 1-N-[(S)-4-amino-2-hydroxybutyryl]-3′,4′-dideoxyneamine. (2) 1-N-[(S)-4-amino-2-hydroxybutyryl]-3′,4′-dideoxyribostamycin. (3) 1-N-[(s)-4-amino-2-hydroxybutyryl]-3′,4′-dideoxykanamycin B. (4) 1-N-[(S)-4-amino-2-hydroxybutyryl]-3′-deoxyneamine. (5) 1-N-[(S)-4-amino-2-hydroxybutyryl]-3′-deoxyribostamycin. (6) 1-N-[(S)-4-amino-2-hydroxybutyryl]-3′-deoxykanamycin B. (7) 1-N-[(S)-4-amino-2-hydroxybutyryl]-3′-deoxy-6′-N-methylkanamycin B. (8) 1-N-[(S)-4-amino-2-hydroxybutyryl]-kanamycin B.

Examples of the pharmaceutically acceptable acid-addition salts of the compound of the above-mentioned general formula (I) according to this invention include the hydrochloride, sulfate, phosphate, acetate, maleate, fumarate, succinate, tartrate, oxalate, citrate, methanesulfonate, ethanesulfonate, and the like.

1-N-[(S)-4-amino-2-hydroxybutyryl]-3′,4′-dideoxyneamine (hereinafter abbreviated as AHB-dideoxyneamine) has the following physical, chemical and biological properties: This compound is a colorless crystalline powder. $[\alpha]_D^{22} + 38°$, (c 0.85, water). This compound shows $^{RF}$3′,4′-dideoxyneamine 0.47 (on paper chromatography with 6:4:3:1 n-butanol-pyridine-water-acetic acid as the development solvent). The AHB-dideoxyneamine is of a lower toxicity to animals and men, as shown by the fact that it shows a $LD_{50}$ of more than 100 mg/kg upon intravenous injection of this compound in mice. In addition, this compound exhibits a antibacterial activity against various gram-positive and gram-negative bacteria, including the kanamycin-resistant strains. The AHB-dideoxyneamine shows higher antibacterial activity than that of the parent substance, 3′,4′-dideoxyneamine, against both sensitive and resistant bacteria. The minimum inhibitory concentrations (meg/ml) of AHB-dideoxyneamine against various microorganisms were determined according to standard serial dilution method using nutrient agar incubation medium at 37° C, the estimation being effected after 18 hours incubation.

An antibacterial spectrum of AHB-dideoxyneamine is shown in the following table together with those of 3′,4′-dideoxyneamine and neamine for comparison.

| Test organisms* | Minimal inhibitory concentration (mcg/ml) | | |
| --- | --- | --- | --- |
| | AHB-dideoxy-neamine | 3′,4′-dideoxy-neamine | Neamine |
| Staphylococcus aureus FDA 209P | 3.12 | 6.25 | 6.25 |
| Sarcine lutea PCI 1001 | 25 | 50 | >100 |
| Bacillus subtilis NRRL B-558 | <0.39 | 0.39 | 0.78 |
| Llebsiella pneumoniae PCI 602 | 6.25 | 25 | 12.5 |
| Klebsiella pneumoniae type 22 #3038 | 12.5 | 25 | >100 |
| Salmonella typhosa T-63 | 1.56 | 3.12 | 3.12 |
| Escherichia coli NIHJ | 3.12 | 12.5 | 12.5 |
| " K-12 | 3.12 | 6.25 | 6.25 |
| " K-12 R-5 | 50 | 50 | >100 |
| " K-12 ML 1629 | 3.12 | 12.5 | >100 |
| " K-12 ML 1630 | 3.12 | 12.5 | >100 |
| " K-12 ML 1410 | 3.12 | 6.25 | 12.5 |
| " K-12 ML 1410 R 81 | 12.5 | 25 | >100 |
| " K-12 LA 290 R 55 | 3.12 | 6.25 | 5.25 |
| " K-12 LA 290 R 56 | 3.12 | 6.25 | 12.5 |
| " K-12 LA 290 R 64 | 3.12 | 12.5 | 6.25 |
| " K-12 C 600 R 135 | 12.5 | 12.5 | 12.5 |
| " K-12 W 677 | 3.12 | 6.25 | 6.25 |
| " K-12 JR 66/W 67 | 12.5 | 25 | >100 |
| " J 5 R 11-2 | 6.25 | 6.25 | >100 |
| Pseudomonas aeruginosa A 3 | 6.25 | 25 | >100 |
| " No.12 | 6.25 | 25 | >100 |
| " GN 315 | >100 | >100 | >100 |
| " TI-13 | 6.25 | 25 | >100 |
| " 99 | 25 | 50 | >100 |
| Proteus rettgeri GN 311 | 25 | 50 | 100 |
| " GN 466 | 12.5 | 25 | 25 |
| Mycobacterium smegmatis ATCC 607** | 6.25 | 25 | 12.5 |

*Agar Agar dilution streak method (nutrient agar, 37° C, 18 hours).
**48 hours.

1-N-[(S)-4-amino-2-hydroxybutyryl]-3′,4′-dideoxyribostamycin (hereinafter abbreviated as AHB-dideoxyribostamycin) has the following properties: 1-N-[(S)-4-amino-2-hydroxybutyryl]-3′,4′-dideoxyribostamycin, namely 3′,4′-dideoxybutirosin B as a monohydrate, shows $[\alpha]_D^{16} + 25°$ (c 1.8 water). $Rf_{butirosin\ B}$ 1.73 (on paper chromatography with 1-butanol-pyridine-water-acetic acid 6:4:3:1;), Rf0.24 (on thin-layer chromatography with silica gel and chloroform-methanol-17% ammonia 1:4:3). [Calcd. for $C_{21}H_{41}N_5O_{10}\cdot H_2O$: C 46.57, H 8.00, N 12.93; Found: C 46.74, H 7.70, N 13.13].

The AHB-dideoxyribostamycin showed strongly enhanced antibacterial activity as compared with that of ribostamycin and 3′,4′-dideoxyribostamycin and was comparable to that of butirosin B. Moreover it was effective against Klebsiella pneumoniae type 22 #3038 and Escherichia coli K-12 JR 66/W 677, which were resistant to butirosin B.

An antibacterial spectrum of AHB-dideoxyribostamycin, butirosin B, 3′,4′-dideoxyribostamycin and ribostamycin is shown in the following table.

| Test organisms* | Minimal inhibitory concentration (mcg/ml) | | | |
| --- | --- | --- | --- | --- |
| | AHB-dideoxy-ribosta-mycin | Butiro-sin B | 3′,4′-di-deoxy-rib-osta-mycin | Rib-osta-mycin |
| Staphylococcus aureus FDA 209P | 1.56 | 1.56 | 3.12 | 3.12 |
| Sarcina lutea PCI 1001 | 25 | 50 | >100 | 100 |
| Bacillus subtilis NRRL B-558 | <0.39 | 0.39 | 1.56 | 3.12 |
| Klebsiella pneumoniae PCI 602 | 0.78 | 0.78 | 3.12 | 1.56 |
| Klebsiella pneumoniae type 22 #3038 | 3.12 | >100 | 6.25 | >100 |
| Salmonella typhosa T-63 | 0.39 | 0.39 | 1.56 | 1.56 |
| Escherichia coli NIHI | 1.56 | 3.12 | 6.25 | 6.25 |
| " K-12 | 1.56 | 0.78 | 3.12 | 3.12 |
| " K-12 R-5 | 6.25 | 6.25 | 100 | 50 |
| " K-12 ML 1629 | 1.56 | 1.56 | >100 | >100 |
| " K-12 ML 1630 | 0.78 | 1.56 | >100 | >100 |
| " K-12 ML 1410 | 0.78 | 0.78 | 6.25 | 3.12 |
| " K-12 ML 1410 R 81 | 1.56 | 3.12 | >100 | >100 |
| " K-12 LA 290 R 55 | 1.56 | 0.78 | 3.12 | 3.12 |
| " K-12 LA 290 R 56 | <0.39 | 0.78 | 1.56 | 3.12 |
| " K-12 LA 290 R 64 | 1.56 | 0.78 | 3.12 | 1.56 |
| " K-12 C 600 R 135 | 0.78 | 0.78 | 3.12 | 1.56 |
| " K-12 W 677 | 0.78 | 0.39 | 3.12 | 1.56 |
| " K-12 JR 66/W 677 | 3.12 | >100 | 6.25 | >100 |
| " J 5 R 11-2 | <0.39 | 1.56 | 100 | >100 |
| Pseudomonas aeruginosa A 3 | 6.25 | 3.12 | 6.25 | >100 |
| " No.12 | 6.25 | 6.25 | 12.5 | >100 |
| " GN 315 | >100 | >100 | >100 | >100 |
| " TI-13 | 12.5 | 25 | 25 | >100 |
| " 99 | 25 | 50 | 50 | >100 |
| Proteus rettgeri GN 311 | 12.5 | 6.25 | 6.25 | 12.5 |
| " GN 466 | 3.12 | 3.12 | 6.25 | 6.25 |
| Mycobacterium smegmatis ATCC 607** | <0.39 | 0.78 | 3.12 | 6.25 |

*Agar dilution streak method (nutrient agar, 37° C, 18 hours).
**48 hours.

The acute intravenous $LD_{50}$ of AHB-dideoxyribostamycin in mice was more than 100 mg/kg. 1-N-[(S)-4- amino-2-hydroxybutyryl]-3',40'-dideoxykanamycin B (hereinafter abbreviated as AHB-dideoxykanamycin B) has the following properties: This compound in a substance in the form of colorless crystalline powder having a decomposition point of 178° C, $[\alpha]_D^{24}+86.8°$ C (c 0.77, water). A ultra-violet absorption spectrum of this compound in solution in water shows only end absorption, and an infra-red absorption spectrum of this compound in a potassium bromide pellet shows main absorption peaks at 3450, 2950, 1630, 1570, 1480, 1385, 1335 and 1030 cm$^{-1}$, from which the existence of an amido linkage in the molecule of this compound can be confirmed.

The AHB-dideoxykanamycin B exhibits a stronger antibacterial activity than those of kanamycin A and 3',4'-dideoxykanamycin B (hereinafter abbreviated as DKB) against various gram-positive and gram-negative bacteria which are sensitive to kanamycin and DKB. In addition, the AHB-dideoxykanamycin B exhibits a high antibacterial activity against drug-resistant strains such as *Staphylococcus aureus, Escherichia coli* and *Pseudomonas aeruginosa* strains which are resistant to kanamycin and DKB.

The AHB-dideoxykanamycin B is of a toxicity as low as that of kanamycin, as shown by the fact that the AHB-dideoxykanamycin B exhibits a LD$_{50}$ value of more than 150 mg/kg upon intravenous injection of this compound in mice.

The minimum inhibitory concentrations (meg/ml) of the AHB-dideoxykanamycin B against various microorganisms were determined according to a standard serial dilution method using nutrient agar incubation medium at 37° C, the estimation being effected after 18 hours incubation.

An antibacterial spectrum of AHB-dideoxykanamycin B is shown in the following table together with those of kanamycin and DKB for comparison.

| Test organisms | Kanamycin | DKB | AHB-dideoxy-B |
|---|---|---|---|
| *Staphylococcus aureus* FDA 209P | 3.12 | 1.56 | 0.78 |
| *Escherichia coli* K-12 | 0.78 | 1.56 | 0.78 |
| " K-12ML1629 | >100 | 3.12 | 0.78 |
| " K-12ML1630 | >100 | 3.12 | 0.78 |
| " K-12ML1410 | 1.56 | 1.56 | 0.78 |
| " K-12ML1410R81 | >100 | 3.12 | 1.56 |
| " LA290R55 | 100 | >100 | 0.78 |
| " LA290R56 | 12.5 | 25 | 0.39 |
| " LA290R64 | 12.5 | 25 | 0.78 |
| " W677 | 1.56 | 1.56 | 0.39 |
| " JR66/W677 | >100 | 100 | 1.56 |
| *Pseudomonas aeruginosa* A3 | >100 | 3.12 | 3.12 |
| " No.12 | 50 | 3.12 | 1.56 |
| " TI-13 | >100 | 3.12 | 3.12 |
| " 99 | >100 | 12.5 | 12.5 |

1-N-[(S)-4-amino-2-hydroxybutyryl]-3'-deoxyneamine (hereinafter abbreviated as AHB-deoxyneamine) has the following properties: This compound is a substance in the form of a colorless crystalline powder, $[\alpha]_D^{20}$ + 86° (c 1, water).

1-N-[(S)-4-amino-2-hydroxybutyryl]-3'-deoxyribostamycin (hereinafter abbreviated as AHB-deoxyribostamycin) has the following properties: This compound is a substance in the form of a colorless crystalline powder. $[\alpha]_D^{20}$ + 38° (c 1, water).

1-H-[(S)-4-amino-2-hydroxybutyryl]-3'-deoxykanamycin B (hereinafter abbreviated as AHB-deoxykanamycin B) has the following properties: This compound is a substance in the form of a colorless crystalline powder. $[\alpha]_D^{20}$ + 90° (c 1, water).

1-N-[(S)-4-amino-2-hydroxybutyryl]-3'-deoxy-6'-N-methylkanamycin B (hereinafter abbreviated as AHB-methyldeoxykanamycin B) has the following properties: This compound is a substance in the form of a colorless crystalline powder. $[\alpha]_D^{20}$ + 93° (c 1, water).

The AHB-deoxyneamine, AHB-deoxyribostamycin, AHB-deoxykanamycin B and AHB-methyldeoxykanamycin B exhibit not only as antibacterial activity as high as that of their parent substances (3'-deoxyneamine, 3'-deoxyribostamycin, and 3'-deoxykanamycin B) against various gram-positive and gram-positive bacteria which are sensitive to these parent substances, but also they exhibit a high antibacterial activity against the kanamycin-resistant strains of *Staphylococcus aureus, Escherichia coli* and *Pseudomonas aeruginosa* as well as against *Klebsiella pneumoniae* and *Salmonella typhosa*. In addition, they are of a toxicity as low as that of their parent substances, as shown by the fact that they exhibit a LD$_{50}$ value of more than 100 mg/kg upon intravenous injection of these compounds in mice.

The minimum inhibitory concentrations (meg/ml) of the AHB-deoxyneamine, AHB-deoxyribostamycin, AHB-deoxykanamycin B and AHB-methyldeoxykanamycin B against various microorganisms were determined according to a standard serial dilution method using nutrient agar incubation medium at 37° C, the estimation being effected after 18 hours incubation.

Antibacterial spectra of the AHB-deoxyneamine, AHB-deoxyribostamycin, AHB-deoxykanamycin B and AHB-methyldeoxykanamycin B are shown in the following table, together with those of 3-deoxyneamine, 3'-deoxyribostamycin and 2'-deoxy-6'-N-methylkanamycin B for comparison.

| Test organisms | AHB-deoxyneamine | 3'-deoxyneamine | AHB-deoxyribostamycin | 3'-deoxyribostamycin | AHB-deoxykanamycin B | 3'-deoxykanamycin B | AHB-methyldeoxykanamycin B | 3'-deoxy-6'-N-methylkanamycin B |
|---|---|---|---|---|---|---|---|---|
| *Staphylococcus aureus* FDA 209P | 3.12 | — | 1.56 | — | 0.78 | — | 0.78 | — |
|  | 3.12 | — | 1.56 | — | 0.78 | — | 0.78 | — |
| *Escherichia coli* ML1629* | 6.25 | 6.25 | 1.56 | >100 | 0.78 | 0.78 | 0.78 | 1.56 |
| " ML1410 | 6.25 | — | 0.78 | — | 0.78 | — | 0.78 | — |
| " LA290 R55* | 6.25 | 100 | 1.56 | >100 | 0.78 | 50 | 0.78 | 50 |
| " W677 | 6.25 | — | 0.78 | — | 1.56 | — | 3.12 | — |
| " JR66/W677 | 6.25 | >100 | 3.12 | >100 | 3.12 | 50 | 3.12 | 50 |
| *Pseudomonas aeruginosa* A3 | 6.25 | — | 1.56 | — | 0.78 | — | 0.78 | — |

-continued

| Test organisms | AHB-deoxy-neamine | 3'-deoxy-neamine | AHB-deoxy-ribosta-mycin | 3'-deoxy-ribosta-mycin | AHB-deoxy-kana-mycin B | 3'-deoxy-kana-mycin B | AHB-methyl-deoxy-kana-mycin B | 3'-deoxy-6'-N-methyl-kana-mycin B |
|---|---|---|---|---|---|---|---|---|
| " No.12 | 6.25 | — | 3.12 | — | 0.78 | — | 0.78 | — |
| " GN315* | >100 | >100 | >100 | >100 | 50 | 100 | 6.25 | 6.25 |

In the above table, the mark * shows the strain is a drug-resistant strain.

1-N-[(S)-4-amino-2-hydroxybutyryl]-kanamycin B (hereinafter abbreviated as AHB-kanamycin B) has the following properties: This compound is a substance in the form of a colorless crystalline powder of a decomposition point of 181°–183° C, $[\alpha]_D^{20}$ + 85° (c 1, water). This substance gives a single spot positive to the ninhydrin reaction and Rf 0.12 on thin-layer chromatography of silica gel (available under a trade name "ART 5721", a product of Merck Company, West Germany) using a solvent system of 4:1:2:1 methanol-chloroform-28% aqueous ammonia-water as the development solvent (kanamycin B shows Rf 0.37 under the same conditions). This substance also gives a single spot at Rf 0.06 on thin layer chromatography using a solvent system of 4:5:2:5 butanol-ethanol-chloroform-17% aqueous ammonia as the development solvent (kanamycin B shows a Rf-value of 0.17 in this case). A ultra-violet absorption spectrum of this substance in water shows only end absorption, and an infra-red absorption spectrum of this substance in a potassium bromide pellet shows main absorption peaks at 3450, 2950, 1650, 1575, 1490, 1385, 1340, 1140 and 1030 cm$^{-1}$, from which the existence of an amido linkage in the molecule of this substance can be confirmed.

The AHB-kanamycin B exhibits a high antibacterial activity not only against various gram-positive and gram-negative bacteria which are sensitive to kanamycins, but also against the drug-resistant strains of *Escherichia coli* and *Pseudomonas aeruginosa*. This substance is also of low toxicity to animals and men, as shown by the fact that the AHB-kanamycin B exhibits a LD$_{50}$ value of more than 100 mg/kg upon intravenous injection of this compound in mice.

The minimum inhibitory concentrations (meg/ml) of the AHB-kanamycin B against various microorganisms were determined according to a standard serial dilution method using a nutrient agar incubation medium at 37° C, the estimation being effected after 18 hours incubation.

An antibacterial spectrum of AHB-kanamycin B is shown in the following table, together with that of kanamycin for comparison.

| | Minimum inhibitory concentrations (mcg/ml) | |
|---|---|---|
| Test organisms | Kana-mycin B | AHB-kana-mycin B |
| *Staphylococcus aureus* FDA 209P | 0.39 | 0.78 |
| *Staphylococcus aureus* Smith | <0.20 | <0.20 |
| *Staphylococcus aureus* Terajima | <0.20 | 0.20 |
| *Sarcina lutea* PCI 1001 | 1.56 | 3.13 |
| *Bacillus anthracis* | <0.20 | <0.20 |
| *Bacillus subtilis* PCI 219 | <0.20 | <0.20 |
| *Bacillus cereus* ATCC 10702 | 0.78 | 1.56 |
| *Corynebacterium bovis* 1810 | 1.56 | 0.39 |
| *Mycobacterium smegmatis* ATCC 607 | 0.78 | 0.78 |
| *Shigella dysenteriae* JS 11910 | 3.13 | 3.12 |
| *Shigella flexneri* 4b JS 11811 | 3.13 | 3.12 |
| *Shigella sonnei* JS 11746 | 1.56 | 1.56 |
| *Salmonella typhosa* T-63 | 0.20 | 0.39 |

-continued

| | Minimum inhibitory concentrations (mcg/ml) | |
|---|---|---|
| Test organisms | Kana-mycin B | AHB-kana-mycin B |
| *Salmonella enteritidis* 1891 | 1.56 | 3.12 |
| *Proetus vulgaris* OX 19 | 0.78 | 1.56 |
| *Klebsiella pneumoniae* PCI 1602 | 0.78 | 0.39 |
| *Klebsiella pneumoniae* 22 #3038 | >100 | 6.25 |
| *Escherichia coli* MIHJ | 0.78 | 0.78 |
| *Escherichia coli* K-12 | 0.78 | 0.78 |
| *Escherichia coli* K-12 R5 | 1.56 | 0.78 |
| *Escherichia coli* K-12 ML 1629 | >100 | 1.56 |
| *Escherichia coli* K-12 ML 1630 | >100 | 1.56 |
| *Escherichia coli* K-12 ML 1410 | 0.78 | 3.13 |
| *Escherichia coli* K-12 ML 1410 R81 | >100 | 1.56 |
| *Escherichia coli* LA290 R55 | 12.5 | 1.56 |
| *Escherichia coli* LA290 R56 | 3.13 | 0.39 |
| *Escherichia coli* LA290 R64 | 3.13 | 0.39 |
| *Escherichia coli* W677 | 0.39 | 0.39 |
| *Escherichia coli* JR66/W677 | >100 | 3.12 |
| *Pseudomonas aeruginosa* A3 | 50 | 6.25 |
| *Pseudomonas aeruginosa* No.12 | 12.5 | 6.25 |
| *Pseudomonas aeruginosa* TI-13 | 100 | 6.25 |
| *Pseudomonas aeruginosa* GN315 | >100 | 50 |
| *Pseudomonas aeruginosa* 99 | >100 | 25 |

The chemical structure of AHB-kanamycin B was confirmed by the following method.

The penta-N-ethoxycarbonyl derivative of this compound was prepared by the usual SHOTTEN-BAUMANN procedure and hydrolyzed in 6N hydrochloric acid at 100° C for 30 minutes. From the hydrolyzates, mono-N-ethoxycarbonyl-2-deoxystreptamine was isolated by resin chromatography of Amberlite CG50 as a colorless powder, m.p. 199°–201° C, $[\alpha]_D^{22}$ + 18° (c 0.22, water).

Anal. Calcd. for $C_9H_{18}N_2O_5 \cdot \frac{1}{2}H_2O$:

C 44.43, H 7.87, N 11.52.

Found: C 44.68, H 7.35, N 11.35.

By application of the TACu method, (see: UMEZAWA, S.; T. TSUCHIYA & K. TATSUTA: Studies on aminosugars. XI. Configurational studies of aminosugar glycosides and aminocyclitols by a copper complex method. Bull. Chem. Soc. Jap. 39: 1235–1243, 1966) the structure of the compound was determined to be 3-N-ethoxycarbonyl-2-deoxystreptamine.

The new compounds of the formula (I) according to this invention are of a lower toxicity to animals and men, as shown by the fact that it shows a LD$_{50}$ value of more than 100 mg/kg upon intravenous injection of the compound in mice. In addition, the new compounds of this invention exhibit a high antibacterial activity against various gram-positive and gram-negative bacteria, including the kanamycin-resistant strains, so that the new compounds of this invention are useful in treatment of infections by gram-positive and gram-negative bacteria. The compounds of this invention may be administered orally, intraperitoneally, intravenously or intramuscularly using any pharmaceutical form known to the art for such administration and in a similar manner to kanamycins. For instance, the compounds of the formula (I) of this invention may be administered orally using any pharmaceutical form known to the art for such oral administration. Examples of pharmaceutical forms for oral administration are powders, capsules, tablets, syrup, and the like. A suitable dose of the compound for the effective treatment of bacterial infections is in a range of 0.25 – 2 g per person a day when it is given orally. It is preferred that said dose should be orally administered in three to four aliquots per day. The compound of this invention may also be administered by intramuscular injection at a dosage of 50 – 200 mg. per person once or twice a day. Moreover, the compound of the invention may be formulated into an ointment for external application which contains the compound of this invention at a concentration of 0.5 – 5% by weight in mixture with a known ointment base such as polyethylene glycol.

According to a second aspect of this invention, moreover, there is provided a process for the production of an 1-N-[(S)-α-hydroxy-ω-aminoacyl] derivative of an aminoglycosidic antibiotic or its deoxy derivative of the following general formula:

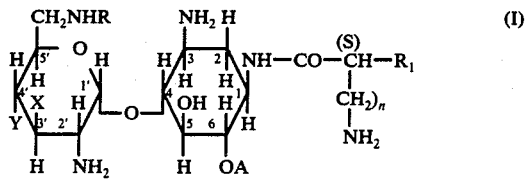

wherein R is a hydrogen atom or an alkyl group of 1–4 carbon atoms; $R_1$ is a hydroxyl group; A is a hydrogen atom or 3-amino-3-deoxy-α-D-glucopyranosyl group of the formula:

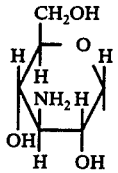

B is a hydrogen atom or β-D-ribofuranosyl group of the formula:

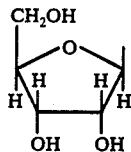

X is a hydrogen atom or hydroxyl group; Y is a hydrogen atom or hydroxyl group; and n is an integer of 2 or 3, provided that both of X and Y do not represent simultaneously the hydroxyl group when A is a hydrogen atom and B is a hydrogen atom or β-D-ribofuranosyl group, which comprises reacting an amino-protected derivative of an aminoglycosidic antibiotic (including its deoxy derivative) of the formula:

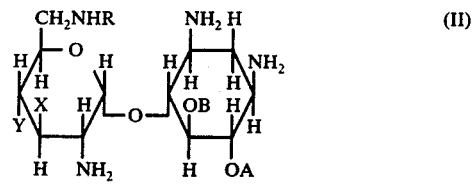

wherein R, A, B, X, and Y have the same meanings as defined above but in which amino-protected derivative at least one of the amino groups other than the 1-amino group as shown by the above formula (II) has been protected by a known amino-protecting group, with an (S)-α-hydroxy-ω-amino acid of the formula:

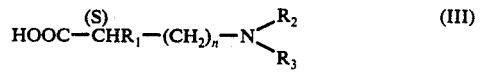

wherein $R_1$ and n have the same meanings as defined above and $R_2$ and $R_3$ are each a hydrogen atom or a known amino-protecting group selected from an acyl group, particularly an alkanoyl group of 1–4 carbon atoms, an alkyloxycarbonyl group of 1–5 carbon atoms, an aralkyloxycarbonyl group, particularly benzyloxycarbonyl group and an aryloxycarbonyl group, or $R_2$ and $R_3$ together form a phthaloyl group, or $R_2$ and $R_3$ together form a group $=CHR_4$ in which $R_4$ is a hydrogen atom, an alkyl group of 1–4 carbon atoms or an aryl group such as phenyl, in a manner known for the acylation to produce the mixed acylation products comprising an 1-N-[(S)-α-hydroxy-ω-aminoacyl] derivative of the amino-protected aminoglycosidic antibiotic represented by the formula:

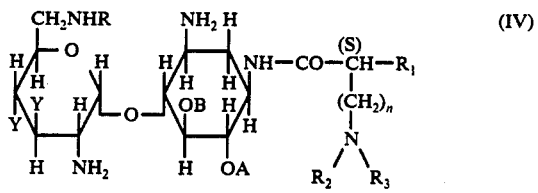

wherein R, $R_1$, $R_2$, $R_3$, A, B, X, and Y are as defined above; but in which aminoacyl derivative at least one of the amino groups other than the 1-amino group of the antibiotic molecule is still protected by the amino-protecting group; treating the mixed acylation products to remove the amino-protecting groups from the acylation products, and then isolating the 1-N-[(S)-α-hydroxy-ω-aminoacyl] derivative of the antibiotic of the formula (I) by chromatographic separation of the acylation products from which the amino-protecting groups have been removed.

With the process according to the second aspect of this invention, it is obvious that the desired compound of the formula (I) would be obtained in a best yield when the amino acid of the formula (III) is reacted with an amino-protected derivative of the aminoglycosidic antibiotic of the formula (II) in which all the amino groups other than the 1-amino group of said antibiotic have been masked by the amino-protecting group. It may be appreciated that kanamycin B and 3',4'-kanamycin B contain five amino groups in each molecule thereof, while neamine, ribostamycin and the deoxy derivatives thereof contain four amino-groups in each molecule thereof. It is possible but is very complicated to prepare such an amino-protected derivative of the aminoglycosidic antibiotic of the formula (II) in which all the amino-groups other than the 1-amino group have been protected by the amino-protecting group while the 1-amino group remains free. Accordingly, we prefer to prepare such an amino-protected derivative of the aminoglycosidic antibiotic of the formula (II) in which only the primary group present in the 6'-position of the antibiotic molecule has been protected by the amino-protecting group, as it is relatively easy and simple to make the 6'-amino group protected preferentially because of the highest reactivity of the 6'-amino group among the amino groups present in the molecule of the antibiotics. Kanamycin B and 3',4'-dideoxykanamycin B contain also the 2'-amino group in the molecule thereof, and the reactivity of the 2'-amino group is lower than that of the 6'-amino group but higher than that of the other amino groups. Accordingly, it is also feasible to prepare amino-protecting derivatives of kanamycin B or 3',4'-dideoxykanamycin B in which either only the 6'-amino group or both the 6'-amino and 2'-amino groups has or have been protected by the amino-protecting group.

To prepare an amino-protected derivative of the antibiotic of the formula (II) which is used as the starting material for the process of this invention, the antibiotic (including its deoxy derivative) of the formula (II) is reacted with a reagent which is known and is commonly used in the conventional synthesis of peptides to introduce a known amino-protecting group. As suitable examples of known amino-protecting groups which are available in this invention, there may be mentioned an alkyloxycarbonyl group such as ethoxycarbonyl, t-butoxycarbonyl and t-amyloxycarbonyl; and cycloalkyloxycarbonyl group such as cyclopentyloxycarbonyl and cyclohexyloxycarbonyl; an aralkyloxycarbonyl group such as benzyloxycarbonyl and p-nitrobenzyloxycarbonyl; an aryloxycarbonyl group such as phenoxycarbonyl and furfuryloxycarbonyl; and an acyl group such as phthaloyl, o-nitrophenoxyacetyl, salicylidene and the like. Such known amino-protecting groups as alkyloxycarbonyl, aralkyloxycarbonyl or aryloxycarbonyl may be shown by a formula —CO—OR$_4$ in which R$_4$ is an alkyl group of 1–4 carbon atoms such as ethyl, t-butyl and t-amyl; a cycloalkyl group such as cyclopentyl and cyclohexyl; an aralkyl group such as benzyl and p-nitrobenzyl; an aryl group such as phenyl or a heterocylic group such as furfuryl. Most preferred as amino-protecting groups are benzyloxy and t-butoxy.

Accordingly, the amino-protected derivative of the antibiotic (II) in which at least one of the amino groups other than the 1-amino group of the antibiotic molecule, particularly the 6'-amino group alone or together with the 2'-amino group has or have been protected by a known amino-protecting group of the formula —CO—OR$_4$ may preferably be prepared in the following manner: an aminoglycosidic antibiotic of the formula (II) is reacted with 0.5 to 3 molar portions of a chloroformate of the formula:

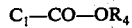  (V)

or a p-nitrophenyl carbonate of the formula:

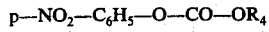  (V')

or an N-hydroxysuccinimide ester of the formula:

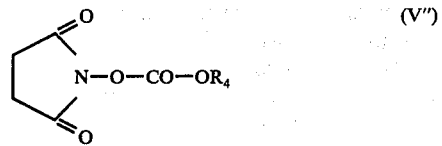  (V")

or an azidoformate of the formula:
$N_3$—CO—OR$_4$   (V''')

in which R$_4$ has the same meaning as defined above, in a suitable solvent such as water, ethyl alcohol, acetone or a mixture thereof under neutral or basic conditions in a way known in the prior art of peptide synthesis. The reaction products so obtained consist of a mixture of various amino-protected derivatives of the antibiotic, comprising a main proportion of an amino-protected derivative of the antibiotic in which only the 6'-amino group of the initial antibiotic molecule has been blocked by the amino-protecting group —CO—OR$_4$ and minor proportions of such amino-protected derivatives of the antibiotics in which the 6'-amino group and one or more of the other amino group(s) have been blocked by the amino-protecting group —CO—OR$_4$, and so on. Accordingly, it is preferable to subject this mixture (said reaction products) to a chromatographic separation using a cation-exchange resin containing carboxylic functions, for example, a copolymer of methacrylic acid with divinylbenzene, such as Amberlite IRC 50 or Amberlite CG 50 (in the form of the ammonium salt), so that there is isolated the amino-protected antibiotic of the formula (II) in which the 6'-amino group alone or possibly together with the 2'-amino group has preferentially be protected by the amino-protecting group.

In carrying out the process of the second aspect of this invention, the amino-protected derivative of the antibiotic of the formula (II) so prepared is reacted with the substituted amino acid of the formula (III) in a manner known for acylation which is commonly conducted in the known synthesis of amides. Thus, the amino-protected derivative of the antibiotic (II) may be acylated by condensing with the substituted amino acid (III) in a solution in dimethylformamide, acetone or tetrahydrofuran under ice-cooling and in the presence of a dehydrating agent such as dicyclohexylcarbodiimide. The substituted amino acid (III) may also be used in the form of its acid chloride, its mixed acid anhydride, its active esters or its azide derivative. Thus, it is also feasible that the substituted amino acid (III) is reacted at first with N-hydroxysuccimide in the presence of dicyclohexylcarbodiimide, so as to prepare its active ester of the formula:

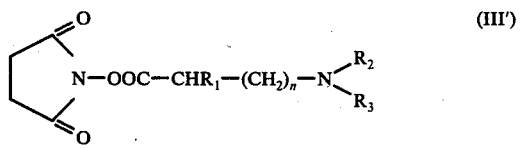  (III')

which is, in turn, reacted with the amino-protected derivative of the antibiotic (II) for the N-acylation of the latter. We prefer that the amino-protected derivative of the antibiotic (II) should be reacted with 0.5 to 3 molar portions of the active ester of the substituted amino acid (III') in a reaction medium consisting of water and an organic solvent such as dimethoxyethane.

Of the substituted amino acid of the formula (III) which is used as the acylating agent in the process of this invention, we prefer to use such a substituted amino acid of the formula (III) in which $R_2$ is a hydrogen atom and $R_3$ is benzyloxycarbonyl group, or such a substituted amino acid of the formula (III) in which $R_2$ and $R_3$ together form a phthaloyl group.

An (S)-α-hydroxy-107-phthalimide acid of the formula:

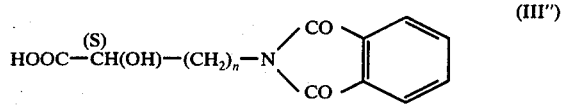

may be prepared by reacting a hydrochloride of an (S)-α,ω-diamino acid of the formula:

wherein $m$ is a whole number of 1 or 2, with a basic copper carbonate in an alkaline aqueous solution to form the copper complex, reacting this copper complex with N-carboethoxyphthalimide to form a copper complex salt of (S)-α-amino-ω-phthalimido acid of the formula:

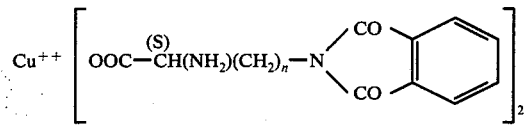

and treating this copper complex salt with diluted hydrochloric acid in methanol to give the corresponding (S)-α-amino-ω-phthalimido acid hydrochloride, and then reacting this hydrochloride with sodium nitrite in aqueous acetic acid produce the desired (S)-α-hydroxy-ω-phthalimido acid (III''). When the above-mentioned (S)-α-amino-ω-phthalimido acid hydrochloride prepared as an intermediate in the above procedure is acetylated with acetic anhydride or acetyl chloride in a known manner, there may be prepared the corresponding (S)-α-acetylamino-ω-phthalimide acid, which may be employed as an (S)-α-substituted-ω-amino acid of the formula (III) in which $R_2$ and $R_3$ together form a phthaloyl group and $R_1$ is acetylamino group.

In the process of the second aspect of this invention, there are produced the mixed acylated products from the condensation reaction of the substituted amino acid (III) with the amino-protected derivative of the antibiotic (II). Thus, the mixed acylated products so produced are usually composed of a mixture of the mono-N-acylated products, the di-N-acylated products and the other N-acylated products, including the desired mono-1-N-acylated product, which are derived from said amino-protected derivative of the antibiotic (II). The mixed acylated products so produced may immediately be treated so as to remove the existing amino-protecting groups therefrom, that is, to convert the amino-protecting groups into hydrogen atoms, respectively. It is also feasible to subject the mixed acylated products to a chromatographic separation, for example using silica gel, so that the unreacted, amino-protected derivative of the antibiotic (II) is removed therefrom, before the conversion of the amino-protecting groups into hydrogen atoms is effected.

The removal of the amino-protecting groups from the acylated products, that is to say, the conversion of the amino-protecting groups of the acylated products into the hydrogen atoms may be effected in various known ways. Thus, when the amino-protecting group is of an alkyloxycarbonyl group, such as t-butoxycarbonyl, a cycloalkyloxycarbonyl group, aryloxycarbonyl group or salicylidene group, the removal of this kind of the amino-protecting group from the acylation products may be effected by subjecting the acylated products to a moderate hydrolysis treatment with a weak acid such as aqueous trifluoroacetic acid, aqueous acetic acid and diluted hydrochloric acid. When the amino-protecting group is of an aralkyloxycarbonyl group such as benzyloxycarbonyl, the removal of this sort of amino-protecting group may be effected by subjecting the acylated products to a hydrogenelysis treatment in the presence of a palladium-carbon catalyst or a to a treatment with hydrobromic acid in acetic acid. The o-nitrophenoxyacetyl group as the amino-protecting group may be removed by a reductive treatment. When the amino-protecting group is phthaloyl group, the removal of the phthaloyl group from the acylated products may be achieved by treating the acylated products with hydrazine hydrate in ethanol under heating. When the acylated products contain different kinds of the amino-protecting groups, the acylated products may be subjected to simultaneous or successive treatments to remove the different amino-protecting groups therefrom. For instance, when the acylated products contain the t-butoxycarbonyl group and the benzyloxycarbonyl group as the amino-protecting group, these groups may be removed simultaneously by treating the acylated products to acidic catalytic hydrogenation with 5% palladium on carbon in 90% trifluoroacetic acid and methanol.

After the removal of the amino-protecting group from the acylated products is carried out, the mixed acylated products from which the amino-protecting group has been removed are then subjected to a chromatographic separation to remove the unreacted materials and to isolate the desired compound of the formula (I). The removal of the unreacted materials may be effected by column chromatography with silica gel. The isolation of the desired compound of the formula (I) from the mixed acylated products may efficiently be achieved by subjecting the acylated products to an ion-exchange chromatography using, for example, a cation-exchange resin containing carboxylic functions, such as Amberlite IRC 50 or Amberlite CG 5C (a product of Rohm & Haas Co., U.S.A.), a weak cation-exchanger such as CM-Sephadex C-25 (a product of Pharmacia Co., Sweden) or CM-cellulose. The eluate from the chromatographic process is collected in fractions, and the antibacterial activity of these fractions is detected using the sensitive bacteria and resistant bacteria as the test microorganisms. Through this detection of the antibacterial activity of each fraction, it is easy to locate the active fractions containing the desired compound of the formula (I) and to recover this desired compound from the active fractions in a manner known for the prior art production and recovery of the known aminoglycosidic antibiotics.

Moreover, for purposes of the isolation and purification of the desired compound of the formula (I) from the mixed acylated products, we have now found it very effective to utilize a ligand-exchange chromatography using an anion-exchange resin such as Dowex 50W x 2 (H cycle) which has been first associated with a metal salt such as cupric chloride, cobaltous chloride, nickel nitrate, ferric chloride, zinc chloride, cadmium chloride and the like and subsequently treated with ammonia or an amine such as methylamine.

According to preferred embodiment of the process of this invention, there is provided a process for the production of an 1-N-[(S)-4-amino-2-hydroxybutyryl] derivtive of 3',4'-dideoxyneamine, 3',4'-dideoxyribostamycin, 3',4'-dideoxykanamycin B, 3'-deoxyneamine, 3'-deoxyribostamycin, 3'-deoxykanamycin B, 3'-deoxy-6'-N-methylkanamycin B or kanamycin B, which comprises reacting N-hydroxysuccinimide ester of (S) -4- benzyloxycarbonylamino-2-hydroxybutyric acid or of (S)-4-tert-butoxycarbonylamino-2-hydroxybutyric acid or of (S)-4-phthalimino-2-hydroxybutyric acid with a starting compound selected from the group consisting of 2',6'-di-N-benzyloxycarbonylated derivatives of 3',4'- dideoxyneamine, 3',4'-dideoxyribostamycin, 3'-deoxyneamine and 3'-deoxyribostamycin; 6'-N-benzyloxycarbonylated derivatives of 3',4'-dideoxykanamycin B, 3'-deoxykanamycin B, 3'-deoxy-6'-N-methylkanamycin B and kanamycin B; 6'-N-tert.-butoxycarbonylated derivatives of 3',4'-dideoxykanamycin B, 3'-deoxykanamycin B, 3'-deoxy-6'-N-methylkanamycin B and kanamycin; 2',6'-di-N-tert.-butoxycarbonylated derivatives of 3',4'-dideoxykanamycin B, 3'-deoxykanamycin B, 3'-deoxy-6'-N-methylkanamycin B, and kanamycin B; and 6'-N-benzylcarboxy-2'-N-tert.-butoxycarbonylated derivatives of 3',4'-dideoxykanamycin B, 3'-deoxykanamycin B, 3'-deoxy-6'-N-methylkanamycin B, and kanamycin B, then treating the resulting acylated reaction products in a known manner to remove the benzyloxycarbonyl group and/or the tert.-butoxycarbonyl groups from the acylated products, and finally separating chromatographically the acylated proucts so treated to isolate the desired 1-N[(S)-4-amino-2-hydroxybutyryl]derivative of the above-mentioned amionglycosidic antibiotics or their deoxy compounds.

The 2',6'-di-N-benzyloxycarbonylated derivatives of the deoxyneamines or deoxyribostamycins may readily be prepared by reacting one of the aforesaid deoxyneamines and deoxyribostamycins with 2 or more molar portions of benzyloxycarbonyl chloride in solution in water at a temperature of 0°–10° C under ice-cooling, passing the reaction mixture through a column of Amberlite IRC 50 and then eluting the resin column with varying concentrations of aqueous ammonia.

The 6'-N-benzyloxycarbonylated derivatives of kanamycin B, or of deoxykananmycin B may be prepared in a high yield in such a manner that the antibiotic in water is reacted with 1-3 molar portions of benzyloxycarbonyl chloride at a temperature of 0°–10° C by adding dropwise the benzyloxycarbonyl chloride under ice-cooling and stirring and that the reaction is completed at room temperature. A main part of the poly-N-benzyloxycarbonylated product, other than the desired 6'-N-benzyloxycarbonylated derivative, can precipitate in the reaction mixture. The reaction mixtue is filtered and the filtrate is washed with ethyl ether. The filtrate is the neutralized and concentrated under reduced pressure, and the concentrated solution is passed through a column of a cation-exchange resin such as Amberlit CG 50 (a product of Rohm & Haas Co., U.S.A., ammonium form) for chromatography to recover a purified form of the 6'-N-benzyloxycarbonylated derivative of the kanamycins. The 6'-N-tert.-butoxycarbonylated derivative of the kanamycins may be prepared in a favorable yield in such a manner that the kanamycin in solution in a mixture of pyridine, water and tri-ethylamine is reacted with 1-3 molar proportions of tert.-butoxycarbonyl azide added dropwise under stirring, the reaction mixture is agitated overnight at room temperature and then concentrated to dryness, the solid so obtained is dissolved in water to prepare an aqueous solution which is then passed through a column of a cation-exchange resin such as Amberlite CG 50 (the ammonium form) for chromatography to recover the desired 6'-N-tert.-butoxycarbonylated derivative of the kanamycins. The 2',6'-di-N-tert.-butoxycarbonylated derivative of kanamycin B or the deoxykanamycin B may be prepared in the same manner as described just above, except that 2–3 molar proportions of tert.-butoxycarbonyl azide is employed. The 6'-N-benzyloxycarbonyl-2'-N-tert.-butoxycarbonylated derivative of kanamycin B or the deoxykanamycin B may be prepared by reacting the previously formed 6'-N-benzyloxycarbonylated derivative with 1-2 molar proportions of tert.-butoxycarbonyl azide. These amino-protected derivatives so prepared may be employed as the starting material in the process without undergoing any purification thereof.

The invention is now illustrated with reference to the following Examples to which this invention is not limited.

EXAMPLE 1

Synthesis of 1-N-[(S)-4-amino-2-hydroxybutyryl]-3',4'-dideoxyneamine (in the formula (I); A=B=R=X=Y=H, $R_1$=OH and $n$=2).

(a) 3,2',6'-tri-N-benzyloxycarbonyl-3',4'-dideoxyneamine (280 mg) was dissolved in anhydrous tetrahydrofuran, and the resulting solution was mixed with a solution in tetrahydrofuran of the active ester of (S)-2-hydroxy-4-phthalimido-n-butyric acid which had previously been prepared by reacting 110 mg of the substituted butyric acid, 50 mg of N-hydroxysuccinimide and 90 mg of dicyclohexylcarbodiimide with each other in anhydrous tetrahydrofuran. The admixture was agitated at ambient temperature overnight. The reaction mixture was filtered to remove the precipitate, and the filtrate was concentrated to dryness to give a solid comprising crude acylated product. This crude product was purified by column chromatography with silica gel. The purified acylated product which was identified as 3,2',6'-tri-N-benzyloxycarbonyl-3',4'-dideoxy-1-N-[(S)-2-hydroxy-4-phthalimidobutyryl] neamine was obtained in a yield of 62% mp 228°–230° C (recrystallized from methanol), $[\alpha]_D^{22} + 32°$ (c1.5, chloroform), IR: 1705, 1690, 1655, 1535 cm$^{-1}$.

Elemental analysis
Calcd. for $C_{48}H_{53}N_5O_{14} \cdot H_2O$: C 61.20, H 5.89, N 7.43
Found: C 61.34, H 5.93, N 7.39.

(b) 200 mg of 3,2',6'-tri-N-benzyloxycarbonyl-3',4'-dideoxy-1-N-((S)-2-hydroxy-4-phthalimidobutyryl) neamine, the product of the above stage (a), was dissolved in 80% aqueous ethanol and then treated with 4% hydrazine hydrate in 80% ethanol-dioxane (1:1) at 60° C for 2 hours to remove the phthaloyl group. The reaction mixture was concentrated to dryness under reduced pressure, and the solid residue obtained was taken up into chloroform. The chloroform solution was washed with water and concentrated to dryness to give the dephthaloylated product, which was, in turn, dissolved in 4 ml of water-dioxane (1:1). The resulting solution was admixed with a small amount of acetic acid and then subjected to hydrogenation with hydrogen in the presence of palladium-carbon in aqueous dioxane (1:1) to remove the benzyloxycarbonyl groups to give the final product, which was purified by a column of CM-Sephadex C-25 (NH$_4$ + form) with ammonia (0–0.5 N). At the concentration of 0.4 N Ammonia, the desired product was eluted, and further treatment gave 1-N-[(S)-4-amino-2-hydroxybutyryl]-3',4'-dideoxyneamine as a monohydrate in a yield of 53%. $[\alpha]_D^{22}$ + 38° (c 0.85, water), IR: 1650, 1560 cm$^{-1}$. RF$_{3',4'}$-dideoxyneamine 0.47 (on paper chromatography with 1butanol-pyridine-water-acetic acid 6:4:3:1).

Elemental analysis

Calcd. for $C_{16}H_{33}N_5O_6 \cdot H_2O$: C 46.93, H 8.62, N 17.10.

Found: C 46.92, H 8.52, N 17.24.

(c) The starting compound used in the above stage (a), namely 3,2'6-tri-N-benzyloxycarbonyl-3',4'-dideoxyneamine was prepared by reacting 3',4'-dideoxyneamine with benzyloxycarbonyl chloride in 70% methanol to give tetra-N-benzyloxycarbonylneamine in a yield of 80%, $[\alpha]_D^{15}$ + 45.4° (c 2, chloroform,) which was then treated with sodium hydride. The tetra-N-benzyloxycarbonylneamine so obtained was dissolved in anhydrous dimethylformamide (DMF) and after displacement of the air in the reaction vessel with nitrogen, 3 molecular equivalents of sodium hydride were added, and the mixture was agitated in an ice bath for 4 hours. The resulting clear solution was neutralized with acetic acid and poured into a mixture of a large amount of chloroform-water. The crude product obtained from the organic layer was purified by column chromatography with silica gel and chloroform-ethanol (20:1) to give tri-N-benzyloxycarbonyl-3',4'-dideoxyneamine-1,6-carbamate in a yield of 62%, mp 107°–110° C, $[\alpha]_D^{25}$ + 58° (c 1.9, chloroform). IR: 1765 cm$^{-1}$ (trans-fused cyclic carbamate[6]). Calcd. for $C_{37}H_{42}N_4O_{11}$: C 61.83, H 5.89, N 7.80; Found: C 61.92, H 5.99, N 7.67.

750 mg of tri-N-benzyloxycarbonyl-3',4'-dideoxyneamine-1,6-carbamate was dissolved in 20 ml of water-dioxane (1:1), and the resulting solution was admixed with 300 mg of barium hydroxide octahydrate. The admixture was agitated at 95° C for 2 hours to effect partial hydrolysis of the carbamate compound. The reaction mixture was filtered to remove the precipitate, and the dioxane was distilled off from the filtrate to give a residue which was then extracted with chloroform. The chloroform extract was washed with water, dried over anhydrous sodium sulfate and then distilled to remove the chloroform. The solid residue so obtained was purified by silica gel column chromatography to yield 3,2',6'-tri-N-benzyloxycarbonyl-3',4'-dideoxyneamine.

EXAMPLE 2

Synthesis of 1-N-[(S)-4-amino-2-hydroxybutyryl]-3',4'-dideoxykanamycin B (in the formula (I); A= 3-amino-3-deoxy-α-D-glucopyranosyl, B=R=X=Y=H, R$_1$=OH, n=2).

(a) Preparation of 6'-N-benzyloxycarbonyl-3',4'-dideoexykanamycin B. 13.53 g (30 millimole) of 3',4'-dideoxykanamycin (abbreviated as DKB) in the form of the free base was dissolved in 135 ml of water, and to this solution was added dropwise 5.61 g (33 millimole) of benzyloxycarbonyl chloride over 1 hour under stirring and under ice-cooling (0°–5° C). After the addition, the mixture was further stirred for 1 hour at ambient temperature and filtered to remove the precipitate. The filtrate was washed with 135 ml of ethyl ether. The aqueous phase was neutralized by addition of aqueous ammonia and then concentrated under reduced pressure. The concentrated solution was passed through a column of 480 ml. of a cation-exchange resin essentially consisting of a copolymer of methacrylic acid and divinylbenzene (available under a trade name "Amberlite CG 50", a product of Rohm & Haas Co., U.S.A. the ammonium form) to effect the adsorption of the benzyloxycarbonylated DKB by the resin. The resin column was washed with water (1920 ml) and then eluted with 0.1N aqueous ammonia. 960 ml of the first running of the eluate was discarded, and the subsequently running fraction of the eluate amounting to 780 ml was collected, concentrated and freeze-dried to give 5.43 g of a colorless powder of 6'-N-benzyloxycarbonyl DKB, mp. 113°–115° C (with decomposition under foaming). Yield 31%.

(b) Production of 1-N-[(S)-4-amino-2-hydroxybutyryl]DKB. 4.04 g (6.9 millimole) of the 6'-N-benzyloxycarbonyl DKB was dissolved in 26 ml of water, and to this solution was added a solution which was prepared by 2.94 g (8 millimole of N-hydroxysuccinimide ester of (S)-4-benzyloxycarbonylamino-2-hydroxybutyric acid in 45 ml of dimethoxyethane. The admixture was stirred at ambient temperature for 90 minutes and then the reaction mixture was concentrated to dryness. The residue was taken up in a volume of water and the aqueous solution was poured into a column of 560 g of silica gel. The elution was conducted using methanol-chloroform-17% aqueous ammonia (4:2:1), and such eluate fractions containing the unreacted materials were discarded. The fractions containing the mixed acylated products were collected and concentrated to give 5.63 g of the mixed acylated products. The mixed acylated products were dissolved in a mixture of 67 ml of glacial acetic acid, 63 ml of methanol and 17 ml of water, and the solution so obtained was admixed with 1.6 g of 5% palladium-carbon and hydrogenated with hydrogen at atmospheric pressure for 4 hours to remove the benzyloxycarbonyl groups of the acylated products. The reaction mixture was filtered to remove the catalyst, and the filtrate was concentrated to under reduced pressure to give 5.20 g of a powder of the acetate of the acylated products comprising 1-N-[(S)-4-amino-2-hydroxybutyryl] DKB acetate. This powder was dissolved in water and the aqueous solution was poured into a column of 250 ml of a cation-exchange resin made of a copolymer of methacrylic acid and divinylbenzene (commercially available as "Amberlite CG 50" ammonium form). The resin column was washed with water (1000 ml) and eluted successively with 0.1N aqueous ammonia (850 ml), 0.3N aqueous ammonia (830 ml), 0.63N aqueous ammonia (830 ml) and 1N aqueous ammonia (830 ml). The eluate was collected in 17 ml fractions. These fractions were tested according to a usual plate assay method for their antibacterial activity using *Bacillus subtilis* PC 1219 sensitive to DKB, and *Escherichia coli* JR 66/W 677 resistant to DKB as the test microorganisms. 320 ml of the fractions which were eluted by using 1N aqueous ammonia and which showed high antibacterial activity to both the above-mentioned strains were combined together and concentrated to dryness to give 301 mg of a powder. This powder was again dissolved in water and the aqueous solution was re-chromatographed by passing into a column of 11 ml of a cation-exchange resin made of a copolymer of methacrylic acid with divinylbenzene (commercially available as "Amberlite CG 50", ammonium form). Thus, the resin column was at first washed with 40 ml of water and then with 90 ml of 0.5N aqueous ammonia, and subsequently the elution was made using 0.75N aqueous ammonia. Such fractions of the eluate which were positive to the ninhydrin reaction and gave a single spot (Rf 0.17) on silica gel thin layer chromatography using butanol-ethanol-chloroform 17% aqueous ammonia (4:5:2:5) were combined together to a total volume of 26 ml and concentrated to dryness to give 61 mg of a colorless crystalline powder of 1-N-[(S)-4-amino-2-hydroxybutyryl]DKB. Yield 1.6%. Decomposition point 178° C, $[\alpha]_D^{24}$ + 86.8° (c 0.77, water).

Elemental analysis
Found: C 47.60, H 8.21, N 14.93%.
Calculated for $C_{22}H_{44}N_6O_{10}$: C 47.81, H 8.03, N 15.21, O 28.95%.

EXAMPLE 3

Synthesis of 1-N-((S)-4-amino-2-hydroxybutyryl)DKB.

6'-N-benzyloxycarbonyl DKB (611 mg, 1.05 millimole) was dissolved in 3.2 ml of water, and the solution so obtained was admixed with a solution of 347 mg (1.05 millimole) of N-hydroxysuccinimide ester of (S)-4-phthalimido-2-hydroxybutyric acid in 3.2 ml of dimethoxyethane. The admixture was processed in the same manner as in Example 2, and the silica gel chromatography gave 480 mg of the mixed acylated products. The mixed acylated products were dissolved in a mixture of 17.5 ml of glacial acetic acid, 14 ml of methanol and 3.5 ml of water, and to the resulting solution was added 120 mg of 5% palladium-carbon. The solution was subjected to catalytic hydrogenation at atmospheric pressure for 2.5 hours to remove the benzyloxycarbonyl groups of the acylated products. The reaction mixture was filtered to remove the catalyst and then concentrated to dryness to give a powder, which was then dissolved in 15 ml of a solution of 10% of hydrazine hydrate in ethanol. The mixture was heated at 90° C for 2 hours under reflux and then concentrated to dryness. The solid so obtained was purified by column chromatography on a cation-exchange resin made of a copolymer of methacrylic acid and divinylbenzene (commercially available as "Amberlite CG 50", ammonium form) in the same manner as in Example 2, to give 6 mg of a white colored powder of 1-N-[(S)-4-amino-2-hydroxybutyryl]DKB. Yield 1.0%.

EXAMPLE 4

Synthesis of 1-N-((S)-4-amino-2-hydroxybutyryl) DKB.

(a) Preparation of 2',6'-di-N-tert.-butoxycarbonyl DKB.

3',4'-dideoxykanamycin B, that is, DKB in the free base form (5 g, 11 millimole) was dissolved in 550 ml of a mixture of pyridine, water and triethylamine (5:3:5), and the resulting solution was admixed with 3.94 g (27.5 millimole) of tert.-butoxycarbonyl azide. The admixture was agitated at ambient temperature for 18 hours. The reaction mixture was concentrated to dryness under reduced pressure. The solid residue so obtained was taken up into water and the aqueous solution was passed into a column of 300 ml of a cationexchange resin made of a copolymer of methacrylic acid with divinylbenzene (commercially available as "Amberlite CG 50", ammonium form) to effect the adsorption of the butoxycarbonylated products by the resin. The resin column was washed with 1000 ml of water and then eluted with 0.1% aqueous ammonia. Such fractions of the eluate which gave a single spot positive to Rydon-Smith reaction and in high-voltage electrophoresis on filter paper were combined together and concentrated to dryness to give 1.45 g of a white colored powder of 2',6'-di-N-tert.-butoxycarbonyl DKB. Yield 24%. The column was then eluted with 0.2% aqueous ammonia to give 2.98 g of 6'-N-tert.-butoxycarbonyl DKB.

(b) Production of 1-N-[(S)-4-amino-2-hydroxybutyryl] DKB.

639 mg (0.98 millimole) of 2',6'-di-N-tert.-butoxycarbonyl DKB, the product of the above stage (a), was dissolved in a mixture of 5 ml of water and 5 ml of dimethoxyethane, and to the resulting solution was added a solution of 375 mg (1.07 millimole) of N-hydroxysuccinimide ester of (S)-4-benzyloxycarbonylamino-2-hydroxybutyric acid in 10 ml of dimethoxyethane. The mixture was stirred at ambient temperature overnight, and the reaction mixture was concentrated to dryness. The solid residue was taken up into 8 ml of 90% aqueous trifluoroacetic acid, and the solution so obtained was agitated for 20 minutes at ambient temperature. The reaction mixture was admixed with 5.6 ml of methanol, 0.6 ml of water and 334 mg of 5% palladiumcarbon. The hydrogenation was conducted with hydrogen at atmospheric pressure for 4.5 hours to remove the benzyloxycarbonyl groups. The reaction mixture was filtered to remove the catalyst, and the filtrate was concentrated under reduced pressure to afford 1.70 g of a powder of the mixed acylation products in the form of the tri-fluoroacetate. This powder was then chromatographed with a column of a cation-exchange resin made of a copolymer of methacrylic acid and divinylbenzene (commercially available as "Amberlite CG 50") in a similar way to Example 2. 110 mg of 1-N-[(S)-4-amino-2-hydroxybutyryl] DKB was obtained in the form of a colorless crystalline powder. Yield 20.4%.

EXAMPLE 5

Synthesis of 1-N-[(S)-4-amino-2-hydroxybutyryl] DKB.

950 mg (1.62 millimole) of 6'-N-benzyloxycarbonyl DKB was dissolved in 85 ml of a mixture of pyridine-water-triethylamine (10:10:1), and the resulting solution was admixed with 256 mg (1.78 millimole) of tert.-butoxycarbonyl azide. The mixture was agitated at ambient temperature for 21 hours and the reaction mixture was concentrated to dryness to give a faint yellow colored powder which comprised the butoxycarbonylated 6'-N-benzyloxycarbonyl DKB. This powder, without being purified, was taken up into a mixture of 5 ml of water and 5 ml of dimethoxyethane, and the solution so obtained was admixed with a solution of 623 mg (1.78 millimole) of N-hydroxysuccinimide ester of (S)-4-benzyloxycarbonylamino-2-hydroxybutyric acid in 20 ml of dimethoxyethane. The mixture was stirred at ambient temperature for 24 hours and then concentrated to dryness. The solid residue obtained was dissolved in a mixture of 13 ml of 90% aqueous trifluoroacetic acid, 9 ml of methanol and 1 ml of water and then hydrogenated with hydrogen at atmospheric pressure for 5 hours in the presence of 640 mg of 5% palladium-carbon added thereto, to remove the tert.-butoxycarbonyl and benzyloxycarbonyl groups which were the amino-protecting groups. The reaction mixture was filtered to remove the catalyst, and the filtrate was concentrated to dryness under reduced pressure. The solid product so obtained was purified by column chromatography with a cation-exchange resin made of a copolymer of methacrylic acid and divinylbenzene (commercially available as "Amberlite CG 50"), to afford 160 mg of 1-N-[(S)-4-amino-2-hydroxybutyryl] DKB in the form of a colorless crystalline powder. Yield 17.9%.

Example 6

Synthesis of
1-N-((S)-4-amino-2-hydroxybutyryl)-3'-deoxyneamine
(in the formula (I); A=B=R=X=H, Y=OH,
$R_1$=OH, n=2).

3'-Deoxyneamine (100 mg) was dissolved in 5 ml of a mixture of water and dioxane (1:2), and the resulting solution was admixed with 230 mg of benzyl p-nitrophenyl carbonate ($C_6H_5CH_2$—OCO—$OC_6H_4NO_2$). The mixture was agitated at 0° C for 6 hours, and the reaction mixture was passed into a column of a cation-exchange resin made of a copolymer of methacrylic acid and divinylbenzene (commercially available as "Amberlite IRC 50"). The resin column was washed with water-dioxane (1:1) and then eluted using water-dioxane (1:1) containing 0 to 0.1N ammonia. Such fractions of the eluate which were positive to the ninhydrin reaction were collected and combined together, and this solution was concentrated to dryness to give a solid which was mainly composed of the di-N-benzyloxycarbonylated 3'-deoxyneamine. Yield 105 mg.

The solid obtained was then taken up into water-tetrahydrofuran (1:1), and the resulting solution was admixed with a solution of the active ester of (S)-4-N-phthalimido-2-hydroxybutyric acid which had previously been prepared by reacting 103 mg of said butyric acid, 45 mg of N-hydroxysuccinimide and 90 mg of dicyclohexylcarbodiimide with each other in anhydrous tetrahydrofuran. The admixture was stirred at ambient temperature overnight, and the reaction mixture was filtered to remove the precipitate deposited. The filtrate was concentrated to dryness to give a solid, which was then dissolved in a mixture of water and dioxane (1:2). The solution was passed into a column of a cation-exchange resin made of a copolymer of methacrylic acid and divinylbenzene (commercially available as "Amberlite IRC 50"), and the resin column was washed with water-dioxane (1:1) and then eluted with water-dioxane (1:1) containing increasing concentrations of ammonia. Such fractions of the eluate which were weakly positive to the ninhydrin reaction were collected, combined together and then concentrated to dryness. The solid residue so obtained was crude mixed acylated products comprising the 1-N-[(S)-4-phthalimido-2-hydroxybutyryl] derivative of the di-N-benzyloxycarbonylated 3'-deoxyneamine.

The solid residue was dissolved in 80% aqueous ethanol and the resulting solution was admixed with a small amount of hydrazine hydrate. The admixture was stirred at 60° C for 2 hours to effect the reaction for removal of the phthaloyl group. The reaction mixture was concentrated to dryness, and the residue was dissolved in a mixture of water-ethanol-toluene to give a solution which was again concentrated to dryness to yield 85 mg of a solid which was mainly composed of a mixture of the di-N-benzyloxycarbonylmono-(S)-4-amino-2-hydroxybutyryl derivative of 3'-deoxyneamine. This solid was then dissolved in a mixture of water-dioxane (1:3) together with a slight amount of acetic acid. The solution so obtained was hydrogenated with hydrogen at 3 atm., in the presence of 5% palladium-carbon, to remove the benzyloxycarbonyl groups from the acylation products. The reaction mixture was then filtered to remove the palladium catalyst, and the filtrate was concentrated to dryness to give a solid.

This solid was dissolved in water and the aqueous solution was filtered and then passed into a column of a weak cation-exchanger essentially consisting of a three-dimensional network gel of dextran bearing carboxymethyl radicals as the weakly cation-exchange functions (commercially available as "CM-Sephadex C-25", a product of Pharmacia Co., Sweden). The molecular sieve agent column was then eluted using 0 to 0.15N aqueous ammonia with increasing concentrations of ammonia. Such fractions of the eluate which were active against Escherichia coli JR66/W677 resistant to DKB were collected, combined together and concentrated to dryness to give 32 mg of a solid. This solid was then purified by ligand-exchange chromatography using such a resin column containing co-ordinated nickel ions which was prepared as follows: 35 ml of a cation-exchange resin essentially consisting of a sulfonated copolymer of styrene and divinylbenzene (commercially available as "Dowex 50W × 2", a product of Dow Chemical Co., U.S.A.) was admixed with 500 ml of a solution which was prepared by dissolving 0.05 mol of nickel acetate in 0.4N aqueous ammonia followed by filtering. The admixture was agitated for 2 hours to give a deeply blue colored resin. 17 ml of this blue colored resin was charged into a column which was then washed with 200 ml of 0.1N aqueous ammonia. Through this resin column so obtained was passed a solution of the above-mentioned solid in 0.1N aqueous ammonia. The resin column was then eluted using 0.1N to 0.15N aqueous ammonia with increasing concentrations of the ammonia. Such fractions of the eluate which were remarkably active against Escherichia coli JR66/W677 were collected, combined together and concentrated to dryness to give 12 mg of a solid which consisted of 1-N-[(S)-4-aminohydroxybutyryl]-3'-deoxyneamine. This was confirmed by the fact that 2'-deoxystreptamine was formed by oxidizing this solid with periodic acid followed by hydrolyzing. $[\alpha]_D^{20} + 86°$ (c 1, water).

Elemental analysis
Found: C 45.38, H 8.31, N 16.52%.
Calculated for $C_{16}H_{23}N_5O_7 \cdot H_2O$: C 45.16, H 8.29, N 16.46%.

EXAMPLE 7

Synthesis of
1-N-[(S)-4-amino-2-hydroxybutyryl]-3'-deoxyribostamycin (in the formula (I); A=R=X=H,
B=β-D-ribofuranosyl, Y=OH, $R_1$=OR, n=2)

The process of Example 6 was repeated using 100 mg of 3'-deoxyribostamycin as the starting material. The above titled compound was obtained in yield of 8.3 mg. $[\alpha]_D^{20} + 38°$ (c 1, water).

EXAMPLE 8

Synthesis of
1-N-[(S)-4-amino-2-hydroxybutyryl]-3',4'-dideoxyribostamycin (in the formula (I); A=R=X=Y=H,
A=β-D-ribofuranosyl, R₁=OH, n=2).

The process of Example 6 was repeated using 100 mg of 3',4'-dideoxyribostamycin as the starting material. The above title compound was obtained in yield of 5 mg. $[\alpha]_D^{16} + 25°$ (c 1.8, water).

EXAMPLE 9

Synthesis of
1-N-((S)-4-amino-2-hydroxybutyryl)-3'-deoxykanamycin B (in the formula (I);
A=3-amino-3-deoxy-α-D-glucopyranosyl,
B=R=X=H, Y=OH, R₁=OH, n=2).

The process of Example 6 was repeated using 100 mg of 3'-deoxykanamycin B as the starting material. The above titled compound was obtained in yield of 11.2 mg. $[\alpha]_D^{20} + 90°$ (c 1, water).

Elemental analysis
Found: C 45.28, H 7.81, N 14.53%.
Calculated for $C_{22}H_{44}N_6O_{11} \cdot H_2O$: C 45.05, H 7.90, N 14.32%.

EXAMPLE 10

Synthesis of
1-N-[(S)-4-amino-2-hydroxybutyryl]-3'-deoxy-6'-N-methylkanamycin B (in the formula (I);
A=3-amino-3-deoxy-α-D-glucopyranosyl, B=X=H,
R=CH₃, Y=OH, R₁=OH, n=2).

The process of Example 6 was repeated using 3'-deoxy-6'-N-methylkanamycin B, of which preparation is described in the "Journal of Antibiotics" Vol. 25, No. 12, pages 743–745 (1972), as the starting material. The above titled compound was obtained in yield of 8.1 mg. $[\alpha]_D + 93°$ (c 1, water).

EXAMPLE 11

Synthesis of 1-N-[(S)-4-amino-2-hydroxybutyryl] kanamycin B (in the formula (I);
A=3-amino-3-deoxy-α-D-glucopyranosyl, B=R=H, X=Y=R₁=OH, n=2).

(a) Preparation of 6'-N-benzyloxycarbonyl-kanamycin B. Kanamycin B is the free base form (5.8 g, 12 millimole was dissolved in 116 ml of water, and to the resulting solution was added dropwise 2.04 g (12 millimole of benzyloxycarbonyl chloride over 1 hour under ice-cooling and stirring. After the addition, the mixture was stirred for 2 hours at ambient temperature. The reaction mixture was filtered to remove the precipitate deposited, and the filtrate was washed with 116 ml of ethyl ether. The aqueous phase was neutralized with aqueous ammonia and then concentrated under reduced pressure. The concentrated solution was then passed into a column of 240 ml of a cation-exchange resin made of a copolymer of methacrylic acid and divinylbenzene (commercially available as "Amberlite CG 50", ammonium form) to make the 6'-N-benzyloxycarbonylated kanamycin B adsorbed by the resin. The resin column was then washed with water (960 ml) and subsequently eluted with 0.1N aqueous ammonia. Such fractions of the eluate which were positive to the Rydon-Smith reaction and gave a single spot in high-voltage electrophoresis on filter paper were collected, combined together and concentrated to dryness to afford 2.7 g of a white powder of 6'-N-benzyloxycarbonyl-kanamycin B. Yield 37g. (b) Production of 1-N-[(S)-4-amino-2-hydroxybutyryl] kanamycin B.

6'-N-benzyloxycarbonyl-kanamycin B, the product of the above stage (a), (815 mg, 1.2 millimole was dissolved in 3.8 ml of water, and the resulting solution was admixed with a solution of 416 mg (1.2 millimole) of N-hydroxysuccinimide ester of (S)-4-phthalimido-2-hydroxybutyric acid in 4.8 ml of dimethoxyethane. The admixture was agitated for 1 hour at ambient temperature and then concentrated to dryness. The solid residue obtained was then taken up into water and the aqueous solution was passed into a column of 90 g of silica gel. The silica gel column was eluted using methanol-chloroform-17% aqueous ammonia (4:2:1) as the developing solvent. Such fractions of the eluate containing the mixed acylated products but free from the unreacted starting materials were collected together and concentrated to dryness to give 510 mg of a solid which was composed of the mixed acylated products comprising 1-N-[(S)-4-phthalimido-2-hydroxybutyryl]-6'-N-benzyloxycarbonyl-kanamycin B.

This solid was dissolved in a mixture of 17.5 ml of glacial acetic acid, 14 ml of methanol and 3.5 ml of water, and the solution obtained was hydrogenated with hydrogen at atmospheric pressure for 2.5 hours in the presence of 120 mg of 5% palladium-carbon added thereto, so that the benzyloxycarbonyl group was removed from the acylated products. The reaction mixture from the hydrogenation was filtered to remove the palladium catalyst, and the filtrate was concentrated under reduced pressure. The solid residue obtained was dissolved in a mixture of 13.9 ml of ethanol and 1.1 ml of hydrazine hydrate, and the resulting solution was heated at 85° C for 2 hours under reflux so that the phthaloyl group was removed. The reaction mixture was concentrated to dryness under reduced pressure to give a solid.

This solid was dissolved in water and the aqueous solution was passed into a column of 30 ml of a cation-exchange resin essentially consisting of a copolymer of methacrylic acid and divinylbenzene (commercially available as "Amberlite CG 50", ammonium form). The resin column was washed with water (150 ml), and the elution was then conducted successively with 0.1N aqueous ammonia (150 ml), 0.3N aqueous ammonia (180 ml) and 0.5N aqueous ammonia (180 ml). The eluate was collected in 3 ml fractions, which were tested by a usual plate assay method for their antibacterial activity using kanamycin B-sensitive *Bacillus subtilis* BCI 219 and kanamycin B-resistant *Bacherichia coli* JR66/W677 as the test microorganisms. Among the fractions which were obtained by eluting with 0.5N aqueous ammonia and showed a high antibacterial activity to both the above-mentioned strains, those fractions which gave a single spot in thin-layer chromatography with silica gel ("ART 5721") as described hereinbefore were combined together and concentrated to dryness under reduced pressure to give 9 mg of a colorless crystalline powder which was 1-N-[(S)-4-amino-2-hydroxybutyryl] kanamycin B. Yield 1.3%. Decomposition point 181°–183° C. $[\alpha]_D^{20} + 85°$ (c 1.01, water).

Elemental analysis
Found: C 44.94, H 7.61, N 14.02%.
Calculated for $C_{22}H_{44}N_6O_{16}$: C 45.20, H 7.59, N 14.38%.

EXAMPLE 12

Synthesis of 1-N-[(S)-4-amino-2-hydroxybutyryl] kanamycin B.

(a) Preparation of 2',6'-di-N-tert.-butoxycarbonyl-kanamycin B.

Kanamycin B in the free base form (5 g, 10.3 millimole) was dissolved in 516 ml of a mixture of pyridine-water-triethylamine (10:10:1), and the resulting solution was admixed with 3.7 g (25.9 millimole) of tert.-butoxycarbonyl azide. The mixture was stirred at ambient temperature for 20 hours, and the reaction mixture was concentrated to dryness under reduced pressure. The solid residue obtained was dissolved in water and the aqueous solution was passed into a column of 200 ml of an ion exchange resin essentially consisting of a copolymer of methacrylic acid and divinylbenzene (commercially available as "Amberlite CG 50"). The resin column was washed with 1000 ml of water and then eluted with 0.1% aqueous ammonia. Such fractions of the eluate which were positive to the Rydon-Smith reaction and gave a single spot in a high-voltage paper electrophoresis were combined together and concentrated to dryness to afford 1.96 g of a white powder of 2', 6'-di-N-tert.-butoxycarbonyl-kanamycin B.

(b) Production of 1-N-[(S)-4-amino-2-hydroxybutyryl]kanamycin B.

2', 6'-di-N-tert.-butoxycarbonyl-kanamycin B, the product of the above stage (a), (683 mg. 1millimole was dissolved in a mixture of 5 ml of water and 5 ml of dimethoxyethane, and the solution obtained was admixed with a solution of 413 mg (1.1 millimole of N-hydroxysuccinimide ester of (S)-4-benzyloxycarbonylamino-2-hydroxybutyric acid in 10 ml of dimethoxyethane. The admixture was stirred at ambient temperature for 18 hours, and the reaction mixture was concentrated to dryness to give a solid which comprised the mixed acylated products. This solid was dissolved in a mixture of 8 ml of trifluoroacetic acid, 5.6 ml of methanol and 0.6 ml of water, and the resulting solution was hydrogenated with hydrogen at atmospheric pressure for 4.5 hours in the presence of 400 mg of 5% palladium-carbon added, so that the tert.-butoxycarbonyl and benzyloxycarbonyl groups were removed from the acylated products. The reaction mixture was filtered to remove the palladium catalyst, and the filtrate was concentrated to dryness under reduced pressure to give a solid. This solid was dissolved in 15 ml of water and the aqueous solution was chromatographed in a similar way to Example II using as a cation-exchange resin a copolymer of methacrylic acid and divinylbenzene (Amberlite CG 50) and aqueous ammonia as the developing solvent. 104 mg of 1-N-[(S)-4-amino-2-hydroxybutyryl]-kanamycin 3 was obtained as a white crystalline powder. Yield 17.8%.

EXAMPLE 13

Synthesis of 1-N-((S)-4-amino-2-hydroxybutyryl)-kanamycin B.

6'-N-Benzyloxycarbonyl-Kanamycin B(1g, 1.62 millimole) was dissolved in 85 ml of a mixture of pyridine-water-triethylamine (10:10:1) to which was then added 256 mg (1.78 millimole) of tert.-butoxycarbonyl azide. The mixture was agitated at ambient temperature for 21 hours, and the reaction mixture was concentrated to dryness under reduced pressure to give 1.27 g of a faint yellow colored powder comprising tert.-butoxycarbonylated 6'-N-benzyloxycarbonyl-kanamycin B. This powder, without being purified, was dissolved in a mixture of 5ml of water and 5 ml of dimethoxyethane to which was subsequently added a solution of 623 mg (1.78 millimole) of N-hydroxysuccinimide ester of (S)-4-benzyloxycarbonylamino-2-hydroxybutyric acid in 20 ml of dimethoxyethane. The mixture was agitated at ambient temperature for 24 hours to effect the acylation. The reaction mixture was then concentrated to dryness and the solid residue was dissolved in a mixture of 13 ml of 90% aqueous trifluoroacetic acid, 9 ml of methanol and 1 ml of water. The solution was subjected to hydrogenation with hydrogen at atmospheric pressure for 5 hours in the presence of 640 mg of 5% palladium-carbon added, so that the tert.-butoxycarbonyl and benzyloxycarbonyl groups were removed from the acylated products. The reaction mixture was filtered to remove the catalyst, and the filtrate was concentrated to dryness under reduced pressure to give a solid product. This solid product was dissolved and chromatographed in a similar way to Example 11 using a cation-exchange resin made of a copolymer of methacrylic acid and divinylbenzene (Amberlite CG 50). 1-N-[(S)-4-amino-2-hydroxybutyryl] kanamycin B was obtained as a white crystalline powder. Yield 176 mg (18.6%).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages conditions.

What we claim is:

1. A compound of the formula:

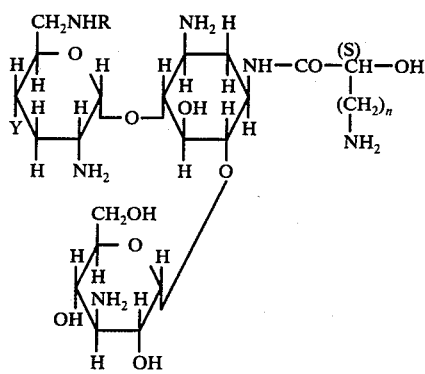

wherein R is hydrogen or alkyl of 1–4 carbon atoms; Y is hydrogen or hydroxyl; $n$ is 2 or 3; and the pharmaceutically acceptable acid addition salts thereof.

2. A compound according to claim 1, wherein Y is hydrogen.

3. A compound according to claim 2, 1-N-[(S)-4-amino-2-hydroxybutyryl]-3', 4'-dideoxykanamycin B.

4. A compound according to claim 1, 1-N-[(S)-4-amino-2-hydroxybutyryl]-3'-deoxykanamycin B.

5. A compound according to claim 1, 1-N-[(S)-4-amino-2-hydroxybutyryl]-3'-deoxy-6'-N-methylkanamycin B.

* * * * *